United States Patent [19]

Smith et al.

[11] Patent Number: 5,550,160
[45] Date of Patent: Aug. 27, 1996

[54] METAL COMPLEXES OF HYDROXYARYL CONTAINING AMINOCARBOXYLIC ACID CHELATING AGENTS

[75] Inventors: Suzanne V. Smith, Caringbah; Richard M. Lambrecht, Birchgrove; Peter F. Schmidt, Cronulla; Fook-Thean Lee, Sylvania, all of Australia

[73] Assignee: Australian Nuclear Science & Technology Organization, Australia

[21] Appl. No.: 99,179

[22] Filed: Jul. 29, 1993

[30] Foreign Application Priority Data

Jul. 31, 1992 [AU] Australia .................. PL3883

[51] Int. Cl.$^6$ .................. A61K 31/215
[52] U.S. Cl. .................. 514/563; 514/425; 562/448; 562/435
[58] Field of Search .................. 562/434, 448, 562/435, 437; 548/546; 514/563, 425

[56] References Cited

U.S. PATENT DOCUMENTS

| | | |
|---|---|---|
| 3,632,637 | 1/1972 | Martell . |
| 3,833,590 | 9/1974 | Dazzi et al. .................. 260/270 |
| 4,479,930 | 10/1984 | Hanatowich . |
| 4,652,440 | 3/1987 | Paik et al. . |
| 4,758,524 | 7/1988 | Bundeser . |

FOREIGN PATENT DOCUMENTS

| | | |
|---|---|---|
| 539726 | 7/1982 | Australia . |
| 81889/87 | 2/1988 | Australia . |
| 20685/88 | 2/1989 | Australia . |
| 0451824 | 10/1991 | European Pat. Off. . |
| 2109407 | 6/1983 | United Kingdom . |
| WO88/08422 | 4/1987 | WIPO . |
| WO87/05030 | 8/1987 | WIPO . |
| WO89/01475 | 2/1989 | WIPO . |
| WO89/01476 | 2/1989 | WIPO . |
| WO89/111475 | 11/1989 | WIPO . |
| WO92/11232 | 7/1992 | WIPO . |

OTHER PUBLICATIONS

Tc–99m–Diethyl–IDA Imaging: "Clinical Evaluation in Jaundiced Patients" S Pauwels, et al, J. Nucl. Med. 1980, 21, 1022–1028.

99mTc–Labelled Trimethylmonoiodo–IDA: "A New Radiopharmaceutical for Hepatobiliary Imaging", UPS Chauhan, et al Nucl Med Biol, 1990, 17, No. 4, 401–408.

"Stabilities of Trivalent Metal Complexes of Phenolic Ligants Related to N,N'-Bis(2–hydroxybenzyl)ethylenediamine-N,n'-diacetic Acid (HBED)", Ramunas J. Motekaitis, et al, Inorg. Chem. 1990, 29, 1463–1467.

"Labeling of Human IgG with Rhodium–105 Using a New Pentadentate Bifuctional Ligand", MRA Pillai, et al, Bioconjugate Chem. 1990, 1, No. 3, 191–197.

A New Bigunctional Chelate, BrMe$_2$HBED: "An Effective Conjugate for Radiometals and Antibodies", Carla J. Mathias, et al, Inorg. Chem. 1990, 29, 1475–1480.

"TMPHG: a Lipophilic Derivative of EHPG for Iron, Gallium–68 and Indium–111 Hepatobiliary Clearance", Susan Madsen, et al, Nucl. Med. Biol., 1991, 18 No. 3, 289–294.

"Targeting Radiopharmaceutical–II. Evaluation of New Trivalent Metal Complexes with Different Overall Charges", Y Sun, et al, Nucl. Med. Biol., 1991, 18 No. 3, 323–330.

"Investigation of Physiochemical and In–Vivo Behavior of Diastereomeric Iron–59, Gallium–68, and Indium–111–EHPG Trivalent Metal Complexes", Susan L. Madsen, The Journal of Nuclear Med. 1990, 31, No. 10, 1662–1668.

"Syntheses of Multidentate Ligands Containing Hydroxypryidyl Donor Groups" Yizhen Sun, et al, Tetrahedron, 47, 1991, No.3, 357–364.

"Stabilities of Gallium (III), Iron (III) and Indium (III) Chelates of Hydroxyaromatic Ligands with Different Overall Charges", Ramgnas J. Motekaitis, et al, Inorg. Chem. 1991, 30, 2737–2740.

"Antibody Labelling with Functionalised Cyclam Macrocyles", J. Richard Morphy, et al, J. Chem. Soc., Chem. Commun., 1988, 156–159.

"Synthesis of C– and N–Functionalised Derivatives of 1,4, 7–Triazacyclonon–one–1,4,7,–triyltriacetic acid (NOTA)", et al. J. Chem Soc, 1990, 2567–2576.

(List continued on next page.)

Primary Examiner—José G. Dees
Assistant Examiner—Samuel Barts
Attorney, Agent, or Firm—Laff, Whitesel, Conte & Saret, Ltd.

[57] ABSTRACT

A physiologically acceptable, radiolabelled compound of general formula

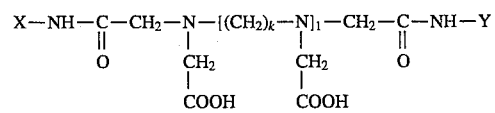

where
k is an integer from 2 to 5
l is an integer from 1 to 5
X and Y are independently selected from phenyl or naphthyl radical each of which can be substituted by one or more amino, mono- or di- substituted amino, halogen, hydroxy, mercapto, nitro, cyano, thiocyano, alkyl, alkoxy, halogenoalkyl, acyl, acylamino, acyloxy, carboxyl, alkoxycarbonyl, carbamoyl, pyridoylamino, N-carboxyalkyl-carbamoyl, sulpho, sulphamoyl, mono- or dialkylated or phenylated sulphamoyl which can also carry one or more substituents R', alkylsulphonyl, alkoxysulphonyl, —(CH$_2$)$_p$NHCOR", —COR" or by an optionally hydroxy-containing phenylsulphonyl or phenoxysulphonyl; or X and Y are independently selected from pyridine or quinoline radical each of which can be substituted by amine, halogen, hydroxy, alkyl, or carbamoyl; where R' is as defined for X and Y; R" is alkyl-L where L is halogen or other leaving group; 2,5-diketo-pyrrolinyl, —Het—CH=CH$_2$ wherein Het is a heterocyclic ring.

6 Claims, 7 Drawing Sheets

OTHER PUBLICATIONS

"Localization of Technetium 99m–Ethylenediamine–N,N'–bis (a –2–hydroxy–5–bromophenyl)acetic Acid", et al, Michael C. Thedarakis, et al, Pharm Sciences, May 1980, 69, No.5, 581–584.

"N,N'Bis(2–hydroxylbenzyl)–1–(4–b romoacetamidobenzyl)–1,2–ethylene–diamine–N,N'–diacetic Acid: A New Bifunctional Chelate for Radiolabeling Antibodies" C. J. Mathias, et al, Bioconjugate Chem., 1, 204–211 (1990), 204–211.

"N–Succinimidyl 5–Trialkylstannyl)–3– pyridinecarboxylates: A New Class of Reagents for Protein Radioidination", Sudha Garg, et al, Biconjugate Chem., 1991, 2, 50–56.

"The Peptide, Analysis, Synthesis, Biology" Bodanszky M. et al, Academic Press, Inc.., Orlando, FL, 1979, 1, 105–196.

"Modern Synthetic Reactions, H.O. House, 2nd Edition, Benjamin, Inc.," Philippines, 1972.

"Principles of Peptide Synthesis", Bodanszky M., Springerverlag, New York, 1984, 9–58.

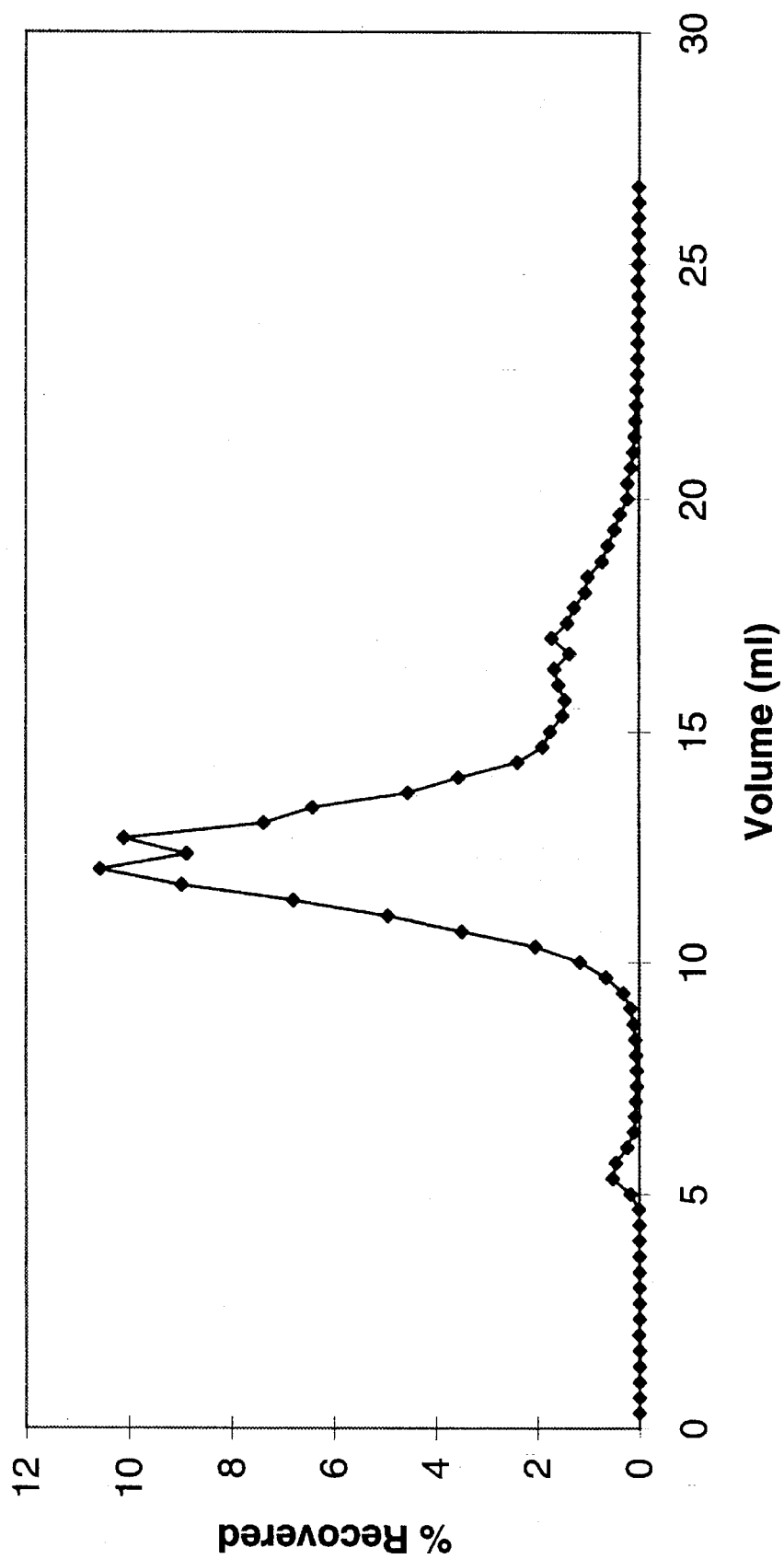
Figure 1 Serum stability of compound (1) with Tc-99m at time = 0 hr.

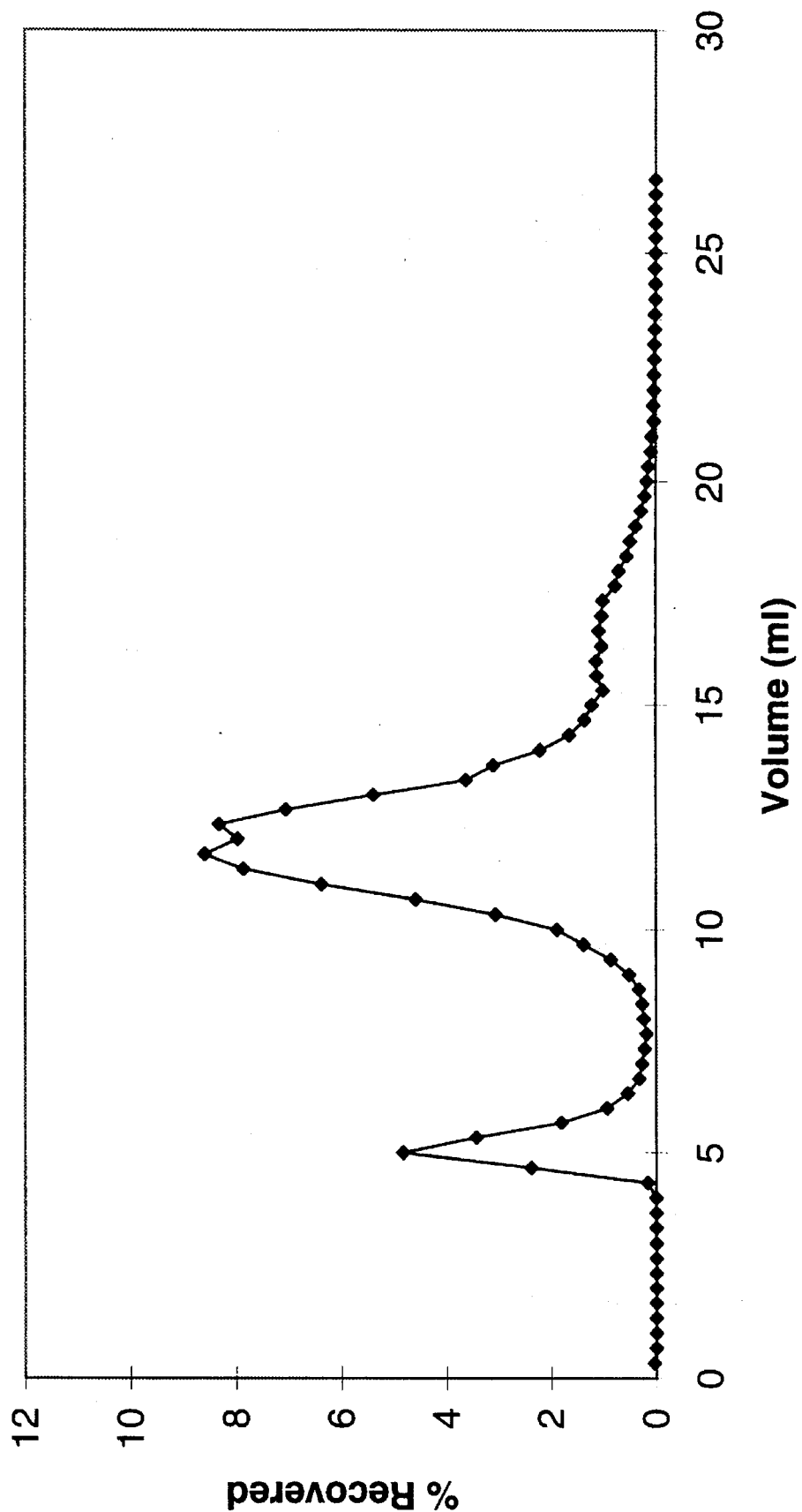
Figure 2  Serum stability of compound (1) with Tc-99m at time = 1 hr.

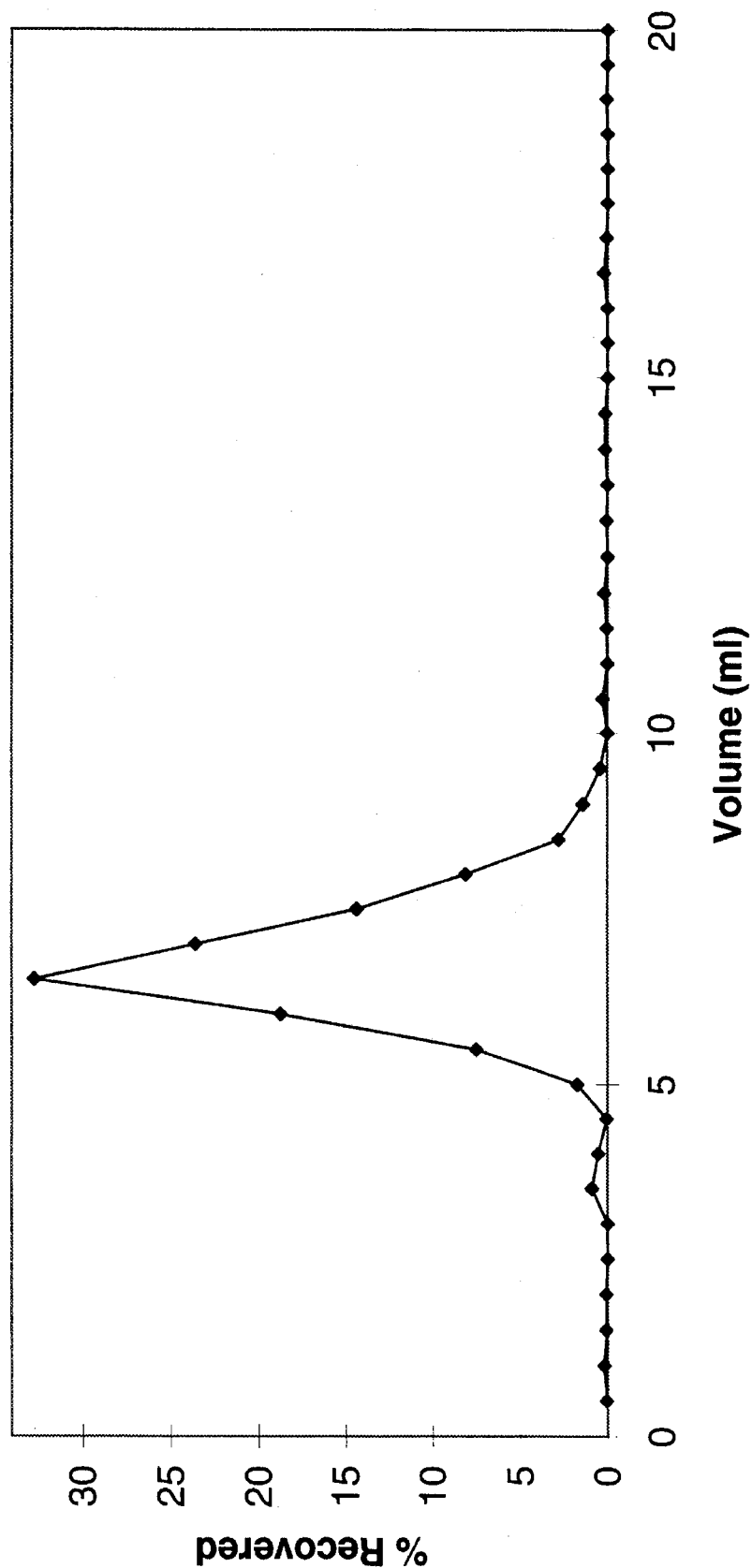
Figure 3  Serum stability of compound (1) with Cu-67 at time = 0 hr.

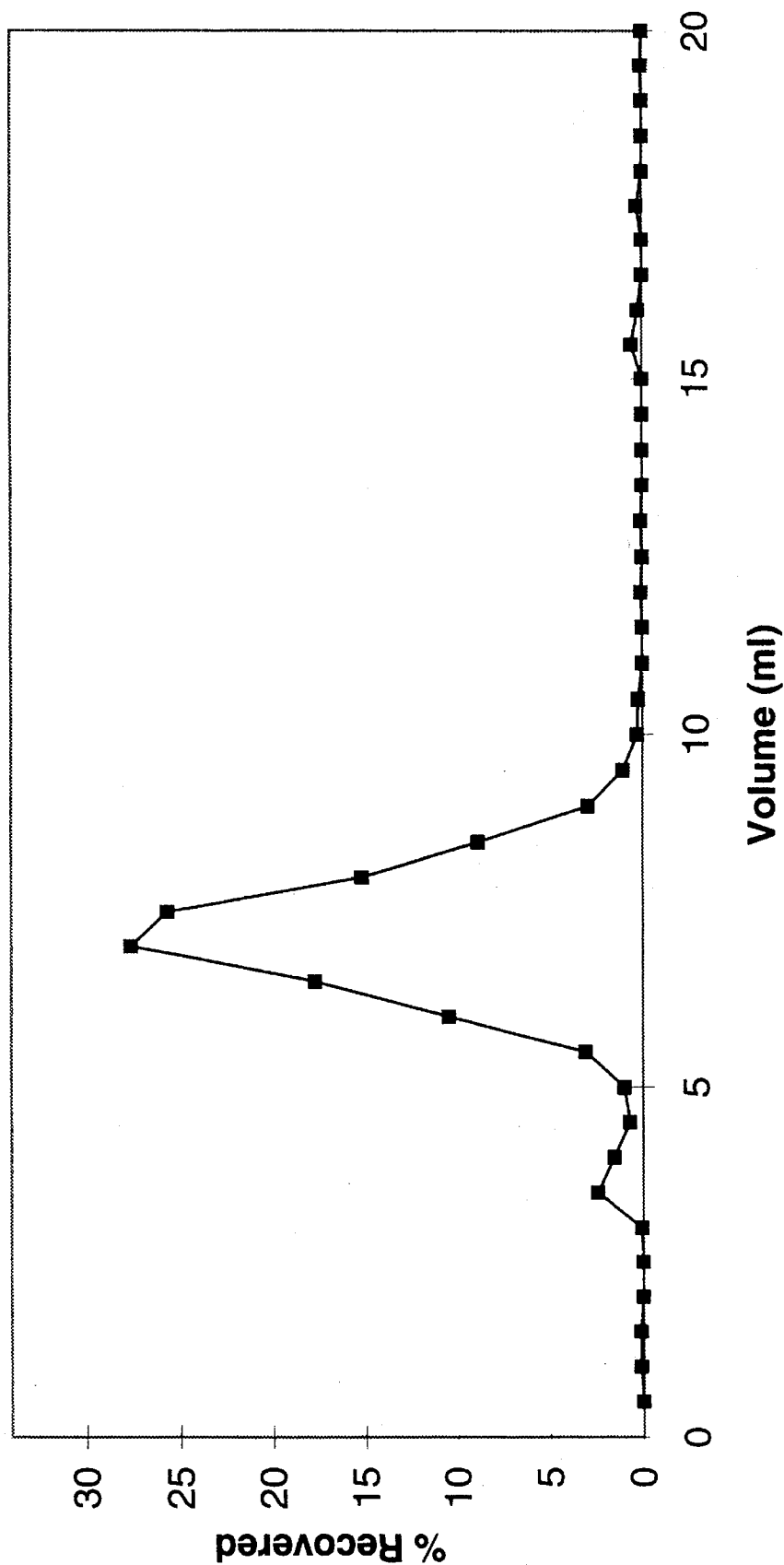
Figure 4  Serum stability of compound (1) with Cu-67 at time = 1 hr.

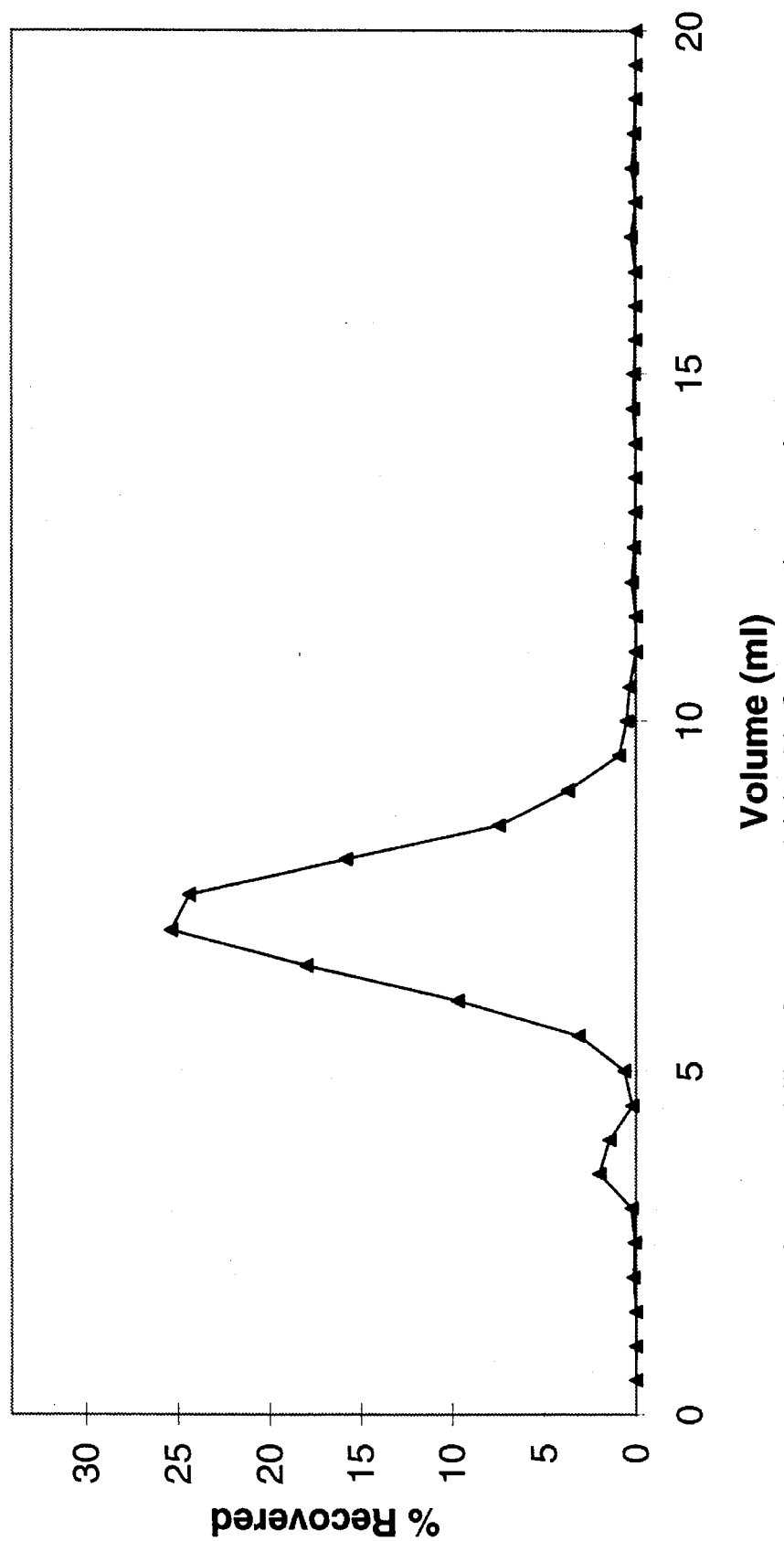
Figure 5  Serum stability of compound (1) with Cu-67 at time = 2 hr.

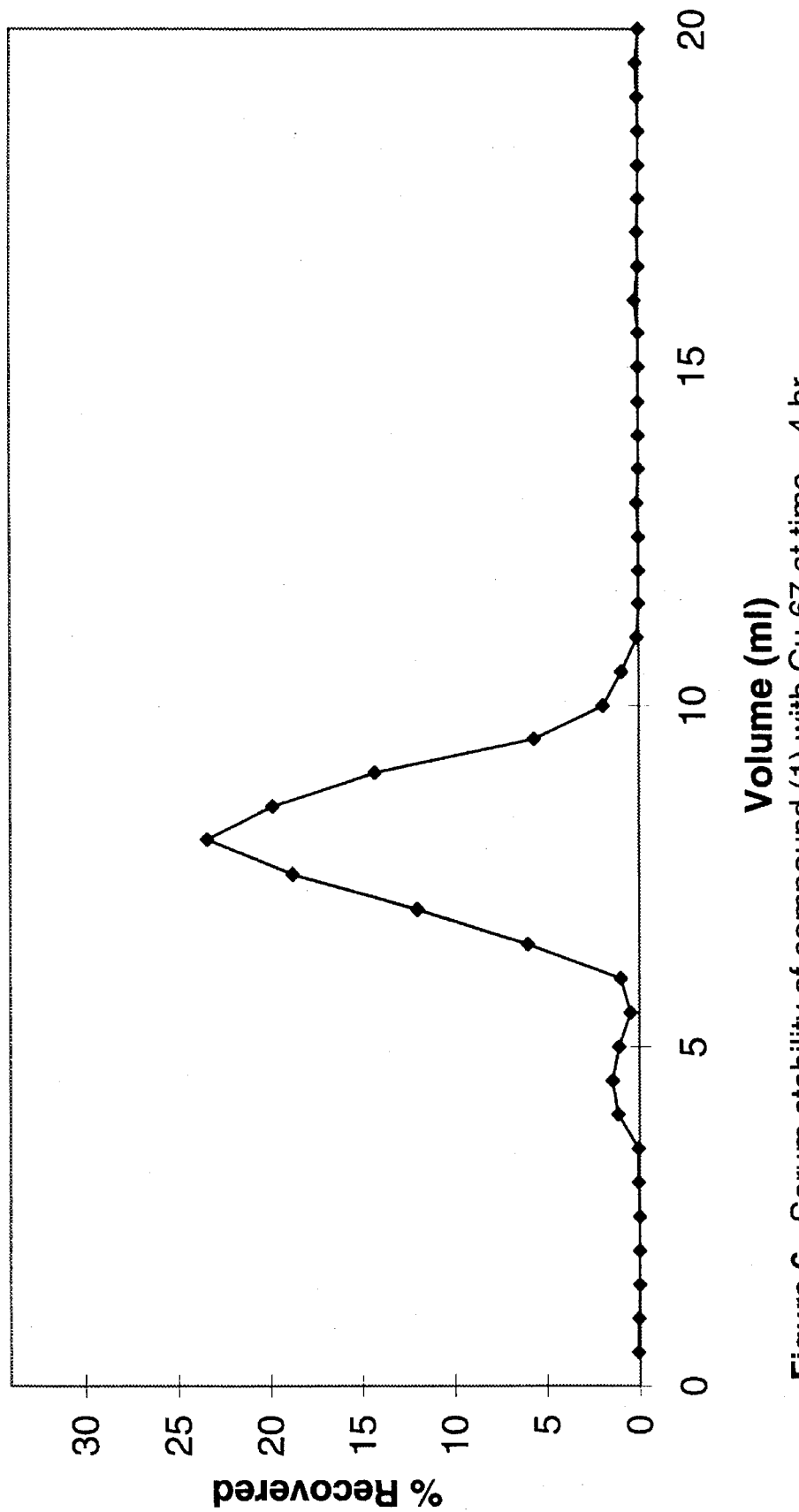
Figure 6 Serum stability of compound (1) with Cu-67 at time = 4 hr.

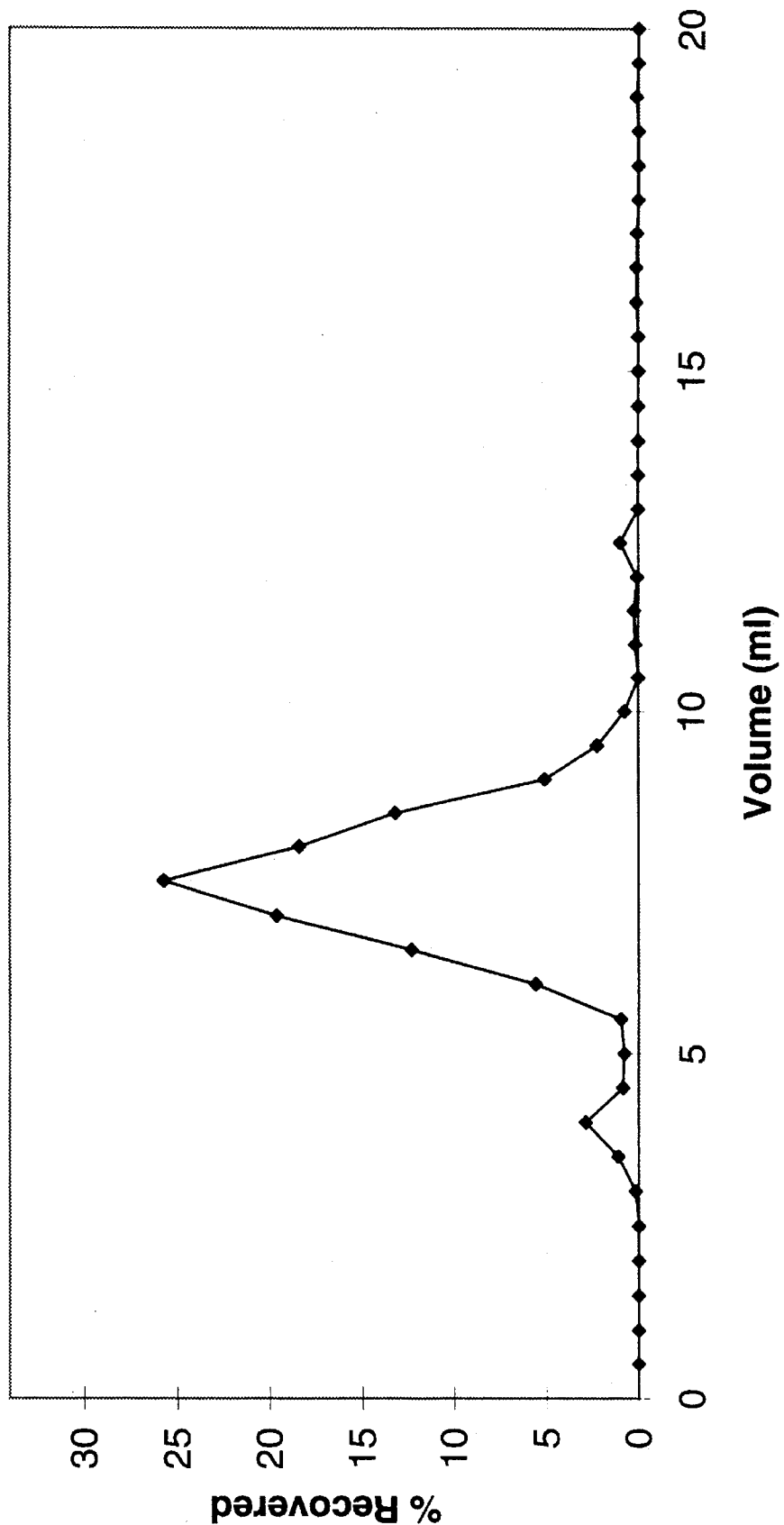
Figure 7 Serum stability of compound (1) with Cu-67 at time = 24 hr.

METAL COMPLEXES OF HYDROXYARYL CONTAINING AMINOCARBOXYLIC ACID CHELATING AGENTS

The present invention relates to radiolabelled derivatives of ethylenediaminetetraacetic acid (EDTA) suitable for use as radiopharmaceutical agents. In particular, the present invention relates to EDTA derivatives, which when complexed with radionuclides may be used as imaging agents for example to assess hepatobiliary function or in radiolabelling of monoclonal antibodies, proteins, peptides oligonucleotides and the like for in vivo imaging or therapy.

U.S. Pat. No. 3,833,590 describes a class of EDTA derivatives which are useful for the control of metal-deficiency phenomena in biological systems. We have found that these derivatives are useful as radiopharmaceutical agents for example, for studying organ function or in radiolabelling of monoclonal antibodies and the disclosure of U.S. Pat. No. 3,833,590 is incorporated herein by reference.

Thus, according to one aspect, the present invention provides radiolabelled compounds of general formula (I)

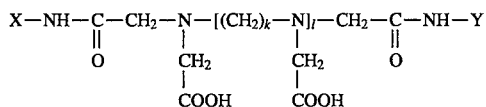

where
k is an integer from 2 to 5
l is an integer from 1 to 5
X and Y are independently selected from phenyl or naphthyl radical each of which can be substituted by one or more amino, halogen, hydroxy, mercapto, nitro, cyano, thiocyano, alkyl, alkoxy, halogenalkyl, acyl, acylamino, acyloxy, carboxyl, alkoxycarbonyl, carbamoyl, pyridoylamino, N-carboxyalkyl-carbamoyl, sulpho, sulphamoyl, mono- or dialkylated or phenylated sulphamoyl which can also carry one or more substitutents R', alkylsulphonyl, alkoxysulphonyl, or by an optionally hydroxy-containing phenylsulphonyl or phenoxysulphonyl; or X and Y are independently selected from pyridine or quinoline radical each of which can be substituted by amine, halogen, hydroxy, alkyl, or carbamoyl; where R' is as defined for X and Y; or pharmaceutically acceptable salts thereof.

Preferably, X and Y are the same. More preferably, there is a donor functional group such as —OH, —SH, —NH, —COOH or the like on the X and Y ring. Preferably, this donor group is ortho to the position of attachment of the ring to the —NH of formula (I).

Compounds of formula (I) and salts thereof, are labelled by nuclides such as technetium-99m ($^{99m}$Tc), copper-64 ($^{64}$Cu) or copper-67 ($^{67}$Cu) and subsequently administered intravenously into a subject for evaluating organ function, for example, the hepatobiliary system and for the purpose of therapy. The specificity for various organs may be achieved by the substitution of hydrophobic or hydrophilic groups on the ring structure at positions X and Y. Preferably, X and Y are each phenyl. For example, specificity for the liver may be achieved by the substitution of hydrophobic groups such as a chloride or a tertiary butyl group on the phenyl ring. The technetium complexes of some of the compounds of formula (I) have shown some specificity, high uptake and prompt excretion into the urine in rats and mice. The compound of formula (I) and salts thereof can also be labelled with radionuclides, such as $^{67}$Ga, $^{111}$In, and other radionuclides from metals such as Y, Co, Re, Fe, Au, Ag, Pb, Bi, Rh, Hg, Ti and Lanthanides such as Sm, Ho or Gd.

The radiolabelling of compounds of formula (I), and salts thereof can be accomplished by using procedures recognised in the art. The radiolabelling of the chelator with copper-67 can be achieved by adding copper in an aqueous acetate solution to a compound of formula (I) in an aqueous solution and incubating for 15 minutes at room temperature.

Alternatively, the radiolabelling of a chelator of formula (I) with technetium, for example, may be achieved by adding a reducing agent such as stannous chloride, to an aqueous solution of a compound of formula (I), followed by reaction with aqueous sodium pertechnetate solution (Na$^{99m}$TcO$_4$). The order of mixing these three components is believed not to be critical. However, preferably the reducing agent is added to the chelator of formula (I). The non-radioactive composition can be supplied to the radiochemists, technicians, radio-pharmacists, doctors and the like for radiolabelling prior to use.

Technetium-99m in the form of an aqueous solution of sodium pertechnetate is readily obtainable from commercially available molybdenum-99technetium-99m generators or alternatively, instant $^{99m}$Tc may be used. $^{64}$Cu is commercially available from Australian Nuclear Science & Technology Organisation and $^{67}$Cu from the US Department of Energy, Brookhaven, USA.

The compounds of formula (I) are obtainable by the reaction of the anhydride of EDTA with one or two equivalents, as desired, of the corresponding amine. The reaction is performed in an inert-gas atmosphere and in the presence of solvent and diluents preferably inert to the reactants. Suitable solvent are aliphatic, aromatic or halogenated hydrocarbons such as benzene, toluene, xylenes, chlorobenzene, chloroform, methylene chloride, ethylene chloride; ethers and ethereal compounds such as dialkyl ether, ethylene glycol mono or -dialkyl ether, THF, dioxane; alkanols such as methanol, ethanol, n-propanol, isopropanol; ketones such as acetone, methyl ethyl ketone; nitriles such as acetonitrile or 2-methoxypropionitrile; N,N-dialkylated amides such as dimethylformamide; dimethylsulphoxide, tetramethylurea; as well as mixtures of these solvents with each other. If the amine or a salt thereof is soluble in water, then the reaction medium may be water at low temperature.

The compounds of formula (I) can be converted to pharmaceutically acceptable salts using art-recognised procedures.

In a second aspect, the present invention provides a diagnostic formulation suitable for labelling with $^{99m}$Tc, $^{188}$Re or $^{186}$Re comprising a compound of formula (I) or a pharmaceutically acceptable salt thereof and a reducing agent in a pharmaceutically acceptable carrier.

In a third aspect, the present invention provides a formulation comprising a radiolabelled compound of formula (I) or a pharmaceutically acceptable salt thereof in a pharmaceutically acceptable carrier.

In a fourth aspect, the present invention provides a method of diagnosis or therapy comprising administering to a subject a radiolabelled compound of formula (I) or a pharmaceutically acceptable salt thereof.

We have further found that the nitro substituents on the X and Y groups of compounds of formula (I) may be further modified to form new compounds of formula (II). The synthesis of these new compounds has provided an opening to a new array of compounds, which have been found to be suitable for radiolabelling of monoclonal antibodies, receptor specific proteins, peptides, or oligonucleotides.

Radiolabelled antibodies are especially useful in medicine, for example, in locating specific tissue types and in the treatment of cell disorders. The labelled antibodies can be used to target metal ions to a specific tissue type, both in vitro and in vivo.

Thus, in a further aspect, the present invention provides novel compounds of formula (II), pharmaceutically acceptable salts and/or radiolabelled complexes thereof

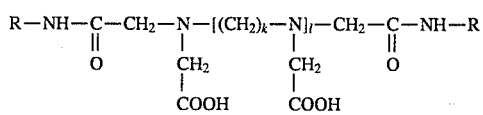

where
k is an integer from 2 to 5
l is an integer from 1 to 5
R is independently selected from

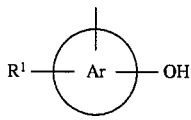

wherein Ar is an aryl or heteroaryl group;
$R^1$ is $-NR^2R^3$ where $R^2$ and $R^3$ are independently selected from hydrogen, $-(CH_2)_p-NH_2$; $-(CH_2)_p-Ar-(CH_2)_n-NH_2$; $-(CH_2)_p-Ar-CO_2H$; $-(CH_2CH_2O)_n-CH_2CH_2NH_2$; $-(CH_2)_p-NCS$, $-(CH_2)_p-Ar-NCS$; or $-(CH_2)_pNHCOR''$, $-COR''$; or
$R^2$ and $R^3$ together with the nitrogen atom to which they are attached form an optionally substituted saturated or partially unsaturated ring optionally containing one or more heteroatoms O, S or N; or
$R^1$ is $-NCS$, $-N=N$ or $-C(=NH)-OCH_3$;
n and m are independently an integer from 0 to 4
p is an integer from 1 to 4;
R'' is alkyl-L where L is halogen or other leaving group; 2,5-diketo-pyrrolinyl, $-Het-CH=CH_2$ wherein Het is an optionally substituted 5 to 6 membered heterocyclic ring containing one or more heteroatoms O, N or S.

Preferably, aryl is phenyl, naphthyl, anthracenyl or the like and heteroaryl is preferably pyridine, quinoline, imidazolyl or the like. Het is preferably pyridine and Het—CH=CH$_2$ is preferably, 2-or 4-vinylpyridine.

In yet a further aspect, the present invention provides a process of preparing compounds of formula (II), which comprises treating the corresponding nitro compound with a catalyst such as palladium/C in the presence of a reducing agent such as sodium borohydride and as required, further derivatising the amino group following procedure known in the art.

Compounds of formula (II) where $R^1$ is mono- or di-substituted amino and where the substituent is substituted alkyl, are readily prepared by treating the amino compound with the appropriate halo-substituted alkyl. For example, compound of formula (II) where $R^1$ is $-NH-CH_2-CH_2-NH_2$ can be prepared by treating a compound of formula (II) where $R^1$ is $NH_2$ with $BrCH_2CH_2NH_2$ in the presence of $NaHCO_3$ or the like.

Compounds of formula (II) where $R^1$ is $-NCS$ is prepared by reacting the amino compound with thiophosgene (see WO87/12631, Kozak et al., Cancer Res. 49, 2639 (1989). Substituted acid halide compounds are produced by reacting a compound of formula (II) where $R^1$ is $NH_2$ with $BrCH_2COBr$ at 4° C. according to the procedure of C. J. Mathias et al., Bioconjugate Chem., 1, 204 (1990). Compounds with an electrophilic moiety can also be prepared by methods known in the art, such as in ACC Chem. Res. 17 202–209 (1984). Compounds with active esters R—C(O)—X can be formed by the procedures of Bodanszky M, *The Peptide, Analysis, Synthesis, Biology*, Ed. E. Gross and J. Meienhofer, Vol 1. pp105–196, Academic Press, Inc., Orlando, Fla. (1979) and Bodanszky M., *Principles of Peptide Synthesis*, pp9–58, Springerverlag, New York, (1984). 2,5-diketo-pyrrolinyl, $-Het-CH=CH_2$ or 2,4-vinylpyridine compounds can be prepared according to the procedure of Morphy et al., J. Chem. Soc., Chem. Commun., 156, (1988). Compounds containing maleimides and succinimide may be prepared by procedures outlined in Y. Arano et al., Bioconjugate Chem., 2, 71 (1991) and S. Garg et al., Bioconjugate Chem., 2, 50, (1991). Other standard procedures are to be found in Modern Synthetic Reactions, H O House, 2nd Edition, Benjamin, Inc. Phillippines, 1972.

The $R^1$ group may be termed the reactive group which provides the point of attachment for a protein such as a monoclonal antibody either directly, ie where $R^1$ is $NH_2$, or through a linker, ie other $R^1$ groups defined above. The isothiocyanate and the halogen functionalised derivatives may be directly linked to a protein (eg. antibody) thiol or amino group. In a structural comparison, it can be seen that $R^1$ is equivalent to a substituent on the X or Y group of compounds of formula (I).

Preferably, the —OH group is ortho to the position of attachment of the phenyl ring to the —NH of formula (II). $R^1$ can be on any other position on the ring.

Compounds of formula (II) provide a method of attachment of radionuclide metal ions such as IN(III), Gd(III), Ga(III), Fe(III), $TcO_4^{3-}$, Cu(II), Ti(IV) and other radionuclides from the Lanthanides, Rhenium, Samarium, Holmium, Yttrium and the like to monoclonal antibodies, receptor specific proteins, peptides or oligonucleotides for in vivo imaging and therapy.

Preferred use of the compounds would be to radiolabel monoclonal antibodies specific for colon, ovarian, lymphoma, breast and/or bladder cancer, with beta emitter radionuclides of metals such as Sm, Ho, Re, Sc, Cu, Pd, Pb, Rh and Y for therapy of above mentioned cancer. A further preferred use is in the radiolabelling of a monoclonal antibody specific for metastasis of colon cancer for diagnosis and therapy.

It is generally preferable to couple the compounds of formula (II) to other molecules such as proteins, peptides, antibodies or carbohydrates to form conjugate compounds for use as radiopharmaceutical agents or cytotoxic agents.

Compounds of formula (II) may be coupled through any thiol, amino, carboxyl, hydroxyl, aldehyde, aromatic or heteroaromatic group present in the protein, peptide, carbohydrate or oligonucleotide.

In particular, the present invention provides a conjugate compound which comprises a compound of formula (II), a radiolabelled complex and/or salt thereof, coupled to an antibody, protein, peptide, carbohydrate or oligonucleotide.

The conjugate compound according to the invention may contain more than one molecule of a compound of formula (II) coupled to any one protein, peptide or carbohydrate molecule. The antibody in the conjugates may be a complete antibody molecule or a fragment thereof or an analogue of either of these, provided that the antibody comprises a specific binding region. The antibody may be humanized monoclonal or a fragment thereof. The antibody may also be a recombinant antibody. The antibody may be specific for any number of antigenic determinants, but is preferably specific for one antigenic determinant.

In another aspect, the present invention provides a pharmaceutical formulation comprising a compound of formula (II), a radiolabelled complex and/or salt thereof in a pharmaceutically acceptable carrier.

In a further aspect, the present invention provides a method of diagnosis or therapy in a subject comprising administering to the subject a compound of formula (II) or a radiolabelled complex and/or salt thereof.

Radiolabelling of proteinaceous materials using bifunctional chelators of the present invention can be conducted in two ways, namely:
(a) prelabelling of chelator followed by conjugation of resultant radiocomplex to proteinaceous material, or
(b) conjugating chelator to protinaceous material for subsequent radiolabelling.

Other suitable applications are:
(a) PET imaging
When chelators of formula (I) or (II) are labelled with $^{64}$Cu (Position 0.278 MeV; half-life 12.70 hours), or $^{62}$Cu (Positron 0.93 MeV; half-life 9.8 minutes), such radiocomplexes may be useful for quantitative dynamic flow measurements of blood flow and bile flow in the hepatobiliary system. Alternatively the chelators may be labelled with Ti-45, a positron emitter (1.04 MeV) with a half life of 3.08 hours.
(b) Radiolabelling monoclonal antibodies with $^{67}$Cu, (Beta and Gamma emitters) for combined radioimmunoscintography (RIS) and radioimmunotherapy (RIT)
(c) Auger emitting agents where a chelator is coupled to an intercalator and labelled with auger emitting isotope such as Fe-59
(d) two step pretargeted radioimmunotherapy A monoclonal antibody with one or more biotin molecules or marker molecules attached is injected into a patient. Once the antibody has cleared from the system and localized to the tumour, a second injection is administered. This second injection involves the radiolabelled chelator attached to a smaller molecule such as avidin or streptavidin which recognises the biotin or marker on the targeted antibody.

Alternatively, the second injection may be avidin or streptavidin and when cleared from the system, the radiolabelled chelator attached to biotin is administered. Both procedures provide amplification of the target site and reduce exposure to normal tissue.

Another two step procedure involves the administration of an antibody-DNA conjugate or antibody-oligonucleotide conjugate followed by targeting with a radiolabelled complementary DNA or complementary oligonucleotide. This procedure also provides amplification of the target site and reduces exposure to normal tissue.
(e) Radiotherapy of Liver metastasis The chelators compound 2 and compound 4 specifically traverse the hepatobiliary system (see data in Tables 2 and 4, Biodistribution of $^{99m}$Tc complex of compound 2 and 4 respectively), and empty into the gastrointestinal tract. When chelators, such as compound 2 and compound 4, are labelled with a therapeutic radionuclide such as $^{67}$Cu, they would be useful for treatment of metastasis of the liver.
(f) Magnetic Resonance Imaging (MRI) agents We envisage the use of these compounds as MRI agents where complexes formed with any pagamagnetic metal ion such as Fe (III) may be used as a contrast agent to enhance images. Also complexes such as these may be attached to a pharmaceutically acceptable carrier for the same purpose. We also envisage the industrial use of these compounds for attachment to solid surfaces such as polymers, electrode surfaces etc. for use in the concentration of metal ions, purification of water or the like.

The present invention also encompasses mixed combinations of radioactive labels on a given monoclonal antibody or a mixture of monoclonals and metal radionuclides attached to one or more different ligands. These would be useful for cancer therapy.

Specific embodiments of the present invention are illustrated by the following examples and drawings. It will be understood, however, that the invention is not confined to specific limitations set forth in the individual examples.

BRIEF DESCRIPTION OF THE DRAWINGS

FIG. 1 is a graph showing serum stability of compound (1) with Tc-99m at time=0 hr.

FIG. 2 is a graph showing serum stability of compound (1) with Tc-99m at time=1 hr.

FIG. 3 is a graph showing serum stability of compound (1) with Cu-67 at time=0 hr.

FIG. 4 is a graph showing serum stability of compound (1) with Cu-67 at time=1 hr.

FIG. 5 is a graph showing serum stability of compound (1) with Cu-67 at time=2 hr.

FIG. 6 is a graph showing serum stability of compound (1) with Cu-67 at time=4 hr.

FIG. 7 is a graph showing serum stability of compound (1) with Cu-67 at time=24 hr.

EXPERIMENTAL

A series of derivatives incorporating carboxyl and phenolate donor groups (1–6) were synthesised by literature method and their radiolabelling characteristic and biological behaviour evaluated. Initial work involved an investigation of radiochemical properties of the $^{99m}$Tc complexes of the ligands and their biodistribution in rats and mice (see Tables 1–6).

Compound No. 3

To a solution of 4-nitro-2-amino-phenol (0.18 g) in acetonitrile (100 ml) was added EDTA anhydride (5.05 g). The reaction mixture was stirred vigorously with reflux under $N_2$ gas overnight. The solid which formed was filtered off while the solution was still warm. The yellow solid was then washed with copious amount of methanol and finally acetone. Yield: 8.92, 81%.

All compounds listed below were prepared in a similar manner. Yields and all spectral data for some compounds are presented in Table A.

| Compound No. | X and Y | Formula |
| --- | --- | --- |
| 1 | 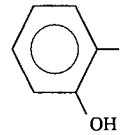 | I |
| 2 | 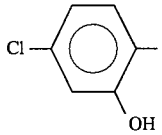 | I |
| 3 | 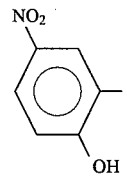 | I |

-continued

| Compound No. | X and Y | Formula |
|---|---|---|
| 4 | t-Bu 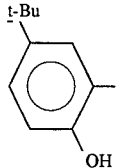 | I |
| 5 | NH₂ 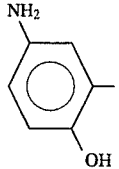 | II |
| 6 | CH₃ 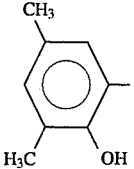 | I |

TABLE A

Physical Data for Selected Compounds

| Cpd (yield %) | Ms[a] | Mpt[b] (°C.) | FTIR[c] (cm⁻¹) | NMR[d] (ppm) |
|---|---|---|---|---|
| No. 1 (95%) | 475 | 204–205 | NH<u>C</u>O, 1708.2<br><u>C</u>OOH, 1635.8<br>O<u>H</u>, 3314.1 | 8.02,6.2H,OH;6.91–6.72,m,6H;Ar;3.46,<br>3.36,s,4H,4H,C<u>H</u>₂CONH,C<u>H</u>₂COOH;2.<br>86,s,4H,NC<u>H</u>₂C<u>H</u>₂; |
| No. 2 (79%) | 543 | 222–224 | NH<u>C</u>O, 1716.9<br><u>C</u>OOH, 1659.0<br>O<u>H</u>, 3331.6 | 9.63,6.2H,OH;8.17,6.01,6.31,d,CH,Ar,0<br>45.3.39,s,4H,4H,C<u>H</u>₂CONH,C<u>H</u>₂COOH<br>2.83,s,4H,NC<u>H</u>₂C<u>H</u>₂; |
| No. 3 (81%) | 564 | 222–226 | NH<u>C</u>O, 1728.4<br><u>C</u>OOH, 1693.9<br>O<u>H</u>, 3299.3 | 9.88,s,2H,OH;9.06,7.89,6.94,d,2H,2H,<br>Ar;3.56,3.52,s,4H,4H,C<u>H</u>₂CONH,C<u>H</u>₂C<br>OOH;2.83,s,4H,NC<u>H</u>₂C<u>H</u>₂; |
| No. 4 (>85%) | 587 | | NH<u>C</u>O, 1708.9<br><u>C</u>OOH, 1658.8<br>O<u>H</u>, 3316.9 | 9.59,s,2H,OH;8.11,6.90,6.75,d,6H,Ar;3<br>42.3,38,s,4H,4H,CH₂CONH,CH₂COO<br>H;2.86,s,4H,NC<u>H</u>₂C<u>H</u>₂,1,21,s,18H,1Bu |
| No. 5 (95%) | 509 | | NHCO, 1740.1<br><u>C</u>OOH, 1683.3<br>OH, 3300 br | 9.33,s,2H, OH,8.41–8.28,m,6H,Ar;5.42<br>5.35,s,4H,4H,C<u>H</u>₂CONH,C<u>H</u>₂COOH;3.<br>80.6,4H,NCH₂CH₂ |

[a]Positive FAB mass spectra were determined of Jeol DX-300 mass spectrometer. MS: parent ion (FAB): m/c, LH⁺,
[b]All melting points are uncorrected.
[c]Diffuse reflectance FT infrared spectra were recorded on BioRad Gigilab FTS-60 in 1% KBr.
[d]The ¹HNMR spectra were determined in d₆DMSO at 298K, on a Jeol Gx-400MHz spectrometer,
"Compound hygroscopic, Decomposes

Preparation of New Compound No. 5

To Palladium/C catalyst (50 mg) in water (10 ml) was added sodium bobohydride (0.24 g) in water (10 ml) under nitrogen gas. To this mixture was then added compound 3 (1.0 g) in ethanol/sodium hydroxide solution (10 ml/1 ml), 8% NaOH) slowly. The mixture was left to stir at room temperature for a further 20 minutes or till the solution becomes clear. To this mixture is added concentrated hydrochloric acid dropwise till all excess sodium borohydride is quenched. Palladium catalyst is filtered off and the filtrate is reduced under vacuum. The pale pink powder is dissolved in a minimum of methanol and any salt remaining filtered off. Yield: 0.85 g; 95%.

Radiolabelling of Chelators with $^{99m}$Tc

A typical method of radiolabelling of the chelator was achieved by dissolving the chelator in a basic solution of saline. The pH was then adjusted to approx. 6 with HCl. Excess stannous chloride was added to the resultant solution followed by one equivalent volume of sodium $^{99m}$TcO₄ (10–50 mCi/ml). Final concentration of the chelator was approx. 1 mg/ml. The efficacy of labelling was determined by ITLC-9G. For each product only one main radiochemical species was observed. Each complex was diluted to 15 μCi/100 μl with saline. In vitro saline stability studies showed the complexes were stable for up to 6 hours. Serum stability studies indicated that no more than 15 per cent of the technetium is lost from the chelator (1) during the first hour at 37° C. (See FIGS. 1 and 2).

Biodistribution studies in rats show that the $^{99m}$Tc complexes are extracted rapidly and efficiently from the blood by the kidney and the liver.

Selected data from biodistribution results of technetium-99m complexes of No. 1, No. 2 and No 4 in the liver, kidney and blood at 3 minutes is tabulated below.

| Compound | Liver | Kidney | Blood |
|---|---|---|---|
| No. 1 | 1.54 | 4.12 | 1.16 |
| No. 2 | 5.93 | 8.90 | 1.32 |
| No. 4 | 7.89 | 4.54 | 1.71 |

The structural variation in this selection of derivatives is the substitution of a chloride atom in No. 2 for a hydrogen atom on both aromatic rings. For No. 3, the substitution of a tertiary butyl group on each aromatic ring. The substitution of these groups make the parent compound more hydrophobic hence there becomes a preference for the liver uptake as opposed to the kidney.

Radiolabelling of Chelators with $^{64}$Cu and $^{67}$Cu

A typical procedure involved the dissolving Cu-67 20 μl of original stock in an acetate buffer (0.2M; pH 4.5) to a total volume of 500 μl. To this solution was added 500 μl of the ligand (20 mg/ml) solution in acetate buffer. The mixture was then left to react at 37° C. for 20 minutes. ITLC confirmed the labelling was greater than >95%.

Serum Stability Studies of Copper-67 Complexes

The serum stability was determined for selected derivatives and typical procedure is as follows.

The ligand (1) was labelled with Cu-67 at a ligand:metal ratio of 4:1. ITLC showed the efficiency of labelling to be >95%. Serum stability studies demonstrated a loss of 4% over the initial 4 hours and no further loss after 24 hours. See FIGS. 3–7.

Biodistribution of Copper-67 Complex of (5)

The biodistribution of the copper-67 complex of ligand (5) was evaluated in balb/c mice (5 animals per time point) at 1, 3, 5, 10, 30 minutes time intervals. The data are presented in Table 7.

The results show that the Cu-67 complex of (5) clears from the kidneys, blood and urine over the 30 minute period. However there appears to be an active uptake of the complex in the liver over the 30 minute period.

Radiolabelling of Protein

Radiolabelling of protein may be achieved by two methods (a). First the chelator may be radiolabelled by a procedure outlined previously. The radiolabelling of the proteinaceous material may be accomplished using a cross-conjugation linker such as EDC ($CH_3CH_2$—N=C=N—$(CH_3)_3$—$NH^+$—$(CH_3)_2$—HCl or the like. For example, to IgG (such as B72.3) in phosphate buffered saline is added the radiolabelled ligand at a molar ratio of 20:1 and EDC in a 1000:1 molar ratio. The mixture is then left to react at 37° C. for 11 hour. The unreacted reagents are removed by size exclusion ultra filtration membrane.

Radiolabelling of Protein with $^{67}$Cu

The radiolabelling of human serum albumin (HSA, Sigma Chemicals) and streptavidin (Sigma Chemicals) and IgG was achieved at values ranging from 0.12–0.16 μCi/μg. The purified radiolabelled IgG was analyzed on HPLC size-exclusion column and fractions collected. Greater than 80% was associated with the main protein peak. No evidence of crosslinking was observed under the labelling conditions used, ie similarly, the chelators can be labelled with a range of radionuclides such as $^{62}$Cu, $^{166}$Ho, $^{153}$Sm, $^{188}$Re, $^{186}$Re and $^{45}$Ti.

(b) The second method involves the conjugation of the chelator to the antibody or proteinaceous material as described but using the unlabelled ligand and prepared in a form suitable for subsequent labelling with a suitable radionuclide. This is the preferred form for preparation of the proteinaceous material in a kit form, suitable for manufacturing.

Formulations of the radiolabelled compounds of formula (I) or (II) are prepared and administered in according to standard techniques. A pharmaceutical formulation of the present invention comprises the active compound together with one or more pharmaceutically acceptable carriers and optionally any other therapeutic ingredient. The formulation may conveniently be prepared in unit dosage form and may be prepared according to conventional pharmaceutical techniques. Additionally, the formulation may comprise one or more accessory ingredients such as diluents or buffers. The effective amount of the active compound will vary both with the route of administration, the condition under treatment and host undergoing treatment.

TABLE 1

| BIODISTRIBUTION OF $^{99m}$TC COMPLEX OF NO. 1[a] | | | | | | | | | |
|---|---|---|---|---|---|---|---|---|---|
| | MEAN 30 SEC | SD | MEAN 1 MIN | SD | MEAN 3 MIN | SD | MEAN 5 MIN | SD | MEAN 10 MIN | SD |
| LIVER | 1.73 | 0.21 | 2.01 | 0.15 | 1.54 | 0.10 | 1.34 | 0.15 | 0.76 | 0.15 |
| SPLEEN | 0.53 | 0.04 | 0.42 | 0.04 | 0.26 | 0.03 | 0.20 | 0.03 | 0.15 | 0.01 |
| KIDNEYS | 6.73 | 0.45 | 6.55 | 0.50 | 4.12 | 0.62 | 2.87 | 0.21 | 2.72 | 0.34 |
| MUSCLE | 0.28 | 0.02 | 0.27 | 0.03 | 0.26 | 0.07 | 0.27 | 0.13 | 0.15 | 0.01 |
| SKIN | 0.37 | 0.03 | 0.43 | 0.05 | 0.49 | 0.04 | 0.53 | 0.06 | 0.40 | 0.10 |
| BONE | 0.31 | 0.03 | 0.32 | 0.03 | 0.26 | 0.02 | 0.25 | 0.07 | 0.19 | 0.02 |
| LUNGS | 1.15 | 0.10 | 1.13 | 0.11 | 0.80 | 0.05 | 0.54 | 0.03 | 0.46 | 0.03 |
| HEART | 0.75 | 0.04 | 0.67 | 0.09 | 0.46 | 0.06 | 0.33 | 0.03 | 0.27 | 0.03 |
| BLOOD | 1.93 | 0.09 | 1.71 | 0.14 | 1.16 | 0.14 | 0.83 | 0.05 | 0.71 | 0.04 |
| STOMACH | 0.14 | 0.08 | 0.28 | 0.14 | 0.32 | 0.28 | 0.11 | 0.01 | 0.12 | 0.03 |
| TOT GIT | 0.27 | 0.02 | 0.34 | 0.03 | 0.59 | 0.19 | 0.79 | 0.08 | 1.22 | 0.16 |
| TAIL | 0.68 | 0.03 | 0.56 | 0.05 | 0.80 | 0.32 | 0.73 | 0.04 | 0.83 | 0.10 |
| BRAIN | 0.14 | 0.30 | 0.09 | 0.03 | 0.06 | 0.02 | 0.05 | 0.01 | 0.04 | 0.01 |
| THYROID | 1.42 | 0.14 | 1.15 | 0.24 | 1.17 | 1.12 | 0.59 | 0.09 | 0.40 | 0.07 |
| EYES | 0.19 | 0.02 | 0.17 | 0.01 | 0.18 | 0.02 | 0.17 | 0.01 | 0.13 | 0.02 |
| PANCREAS | 0.49 | 0.08 | 0.51 | 0.11 | 0.44 | 0.19 | 0.44 | 0.18 | 0.30 | 0.02 |
| THYMUS | 0.38 | 0.04 | 0.35 | 0.04 | 0.27 | 0.03 | 0.19 | 0.03 | 0.14 | 0.01 |

[a]Australian Albino Wistar Rats, % Injected dose per gram (X ± SD). Average of 5 animals per time point.

TABLE 2

BIODISTRIBUTION OF $^{99m}$TC COMPLEX OF NO. 2[a]

| | MEAN 30 SEC | SD | MEAN 1 MIN | SD | MEAN 3 MIN | SD | MEAN 5 MIN | SD | MEAN 10 MIN | SD |
|---|---|---|---|---|---|---|---|---|---|---|
| LIVER | 4.61 | 0.69 | 6.28 | 1.07 | 5.93 | 0.73 | 3.93 | 0.66 | 1.89 | 0.36 |
| SPLEEN | 0.62 | 0.04 | 0.58 | 0.03 | 0.33 | 0.03 | 0.25 | 0.04 | 0.16 | 0.03 |
| KIDNEYS | 6.42 | 0.45 | 8.37 | 0.63 | 8.90 | 0.73 | 7.26 | 2.45 | 3.35 | 0.54 |
| MUSCLE | 0.22 | 0.03 | 0.24 | 0.01 | 0.20 | 0.03 | 0.16 | 0.02 | 0.11 | 0.02 |
| SKIN | 0.29 | 0.02 | 0.45 | 0.07 | 0.42 | 0.02 | 0.35 | 0.02 | 0.33 | 0.05 |
| BONE | 0.34 | 0.03 | 0.37 | 0.03 | 0.25 | 0.03 | 0.19 | 0.02 | 0.15 | 0.03 |
| LUNGS | 1.20 | 0.09 | 1.17 | 0.14 | 0.79 | 0.06 | 0.59 | 0.02 | 0.48 | 0.09 |
| HEART | 0.87 | 0.11 | 0.93 | 0.07 | 0.46 | 0.02 | 0.36 | 0.03 | 0.28 | 0.05 |
| BLOOD | 2.79 | 0.33 | 2.77 | 0.20 | 1.32 | 0.09 | 0.94 | 0.08 | 0.77 | 0.16 |
| STOMACH | 0.41 | 0.10 | 0.68 | 0.46 | 2.08 | 3.10 | 0.98 | 0.94 | 0.90 | 1.51 |
| TOT GIT | 0.48 | 0.12 | 0.58 | 0.08 | 1.56 | 0.25 | 2.27 | 0.19 | 3.18 | 0.71 |
| TAIL | 0.81 | 0.22 | 0.66 | 0.09 | 0.64 | 0.07 | 1.16 | 0.78 | 0.55 | 0.08 |
| BRAIN | 0.14 | 0.01 | 0.09 | 0.01 | 0.06 | 0.01 | 0.04 | 0.01 | 0.03 | 0.01 |
| THYROID | 1.41 | 0.36 | 1.71 | 0.66 | 0.81 | 0.18 | 0.58 | 0.14 | 0.44 | 0.12 |
| EYES | 0.11 | 0.01 | 0.15 | 0.03 | 0.12 | 0.02 | 0.10 | 0.02 | 0.10 | 0.02 |
| PANCREAS | 0.49 | 0.06 | 0.66 | 0.16 | 0.44 | 0.17 | 0.52 | 0.34 | 0.27 | 0.04 |
| THYMUS | 0.39 | 0.05 | 0.37 | 0.08 | 0.27 | 0.04 | 0.17 | 0.02 | 0.15 | 0.03 |

[a]Australian Albino Wistar Rats, % Injected dose per gram (X ± SD). Average of 5 animals per time point.

TABLE 3

BIODISTRIBUTION OF $^{99m}$TC COMPLEX OF NO. 3[a]

| | MEAN 30 SEC | SD | MEAN 1 MIN | SD | MEAN 3 MIN | SD | MEAN 5 MIN | SD | MEAN 10 MIN | SD |
|---|---|---|---|---|---|---|---|---|---|---|
| LIVER | 1.43 | 0.03 | 1.61 | 0.18 | 1.61 | 0.19 | 1.24 | 0.20 | 0.92 | 0.16 |
| SPLEEN | 0.49 | 0.06 | 0.42 | 0.05 | 0.29 | 0.03 | 0.23 | 0.03 | 0.17 | 0.01 |
| KIDNEYS | 3.92 | 0.22 | 4.63 | 0.64 | 4.27 | 1.12 | 3.00 | 0.31 | 2.10 | 0.21 |
| MUSCLE | 0.26 | 0.02 | 0.24 | 0.03 | 0.23 | 0.04 | 0.21 | 0.02 | 0.22 | 0.06 |
| SKIN | 0.49 | 0.06 | 0.43 | 0.07 | 0.58 | 0.11 | 0.64 | 0.08 | 0.63 | 0.04 |
| BONE | 0.30 | 0.03 | 0.29 | 0.04 | 0.30 | 0.11 | 0.29 | 0.08 | 0.22 | 0.04 |
| LUNGS | 1.24 | 0.16 | 1.04 | 0.12 | 0.87 | 0.04 | 0.72 | 0.06 | 0.57 | 0.07 |
| HEART | 0.78 | 0.11 | 0.65 | 0.05 | 0.55 | 0.06 | 0.45 | 0.05 | 0.34 | 0.02 |
| BLOOD | 2.10 | 0.10 | 1.83 | 0.17 | 1.37 | 0.14 | 1.17 | 0.11 | 0.86 | 0.05 |
| TAIL | 0.85 | 0.30 | 2.43 | 3.83 | 0.63 | 0.10 | 0.84 | 0.14 | 0.84 | 0.07 |
| BRAIN | 0.18 | 0.04 | 0.14 | 0.03 | 0.09 | 0.02 | 0.08 | 0.01 | 0.05 | 0.01 |
| THYROID | 1.11 | 0.22 | 1.14 | 0.36 | 0.92 | 0.10 | 0.70 | 0.24 | 0.63 | 0.04 |
| EYES | 0.20 | 0.03 | 0.23 | 0.05 | 0.23 | 0.01 | 0.17 | 0.03 | 0.18 | 0.05 |
| PANCREAS | 0.47 | 0.07 | 0.41 | 0.09 | 0.38 | 0.07 | 0.42 | 0.13 | 0.21 | 0.01 |
| THYMUS | 0.38 | 0.03 | 0.34 | 0.03 | 0.32 | 0.06 | 0.25 | 0.04 | 0.20 | 0.06 |

[a]Australian Albino Wistar Rats, % Injected dose per gram (X ± SD). Average of 5 animals per time point.

TABLE 4

BIODISTRIBUTION OF $^{99m}$TC COMPLEX OF NO. 4[a]

| | MEAN 30 SEC | SD | MEAN 1 MIN | SD | MEAN 3 MIN | SD | MEAN 5 MIN | SD | MEAN 10 MIN | SD |
|---|---|---|---|---|---|---|---|---|---|---|
| LIVER | 6.83 | 0.51 | 8.03 | 0.95 | 7.89 | 0.57 | 7.39 | 1.20 | 4.90 | 1.06 |
| SPLEEN | 0.93 | 0.12 | 0.80 | 0.05 | 0.42 | 0.05 | 0.32 | 0.05 | 0.27 | 0.05 |
| KIDNEYS | 5.57 | 0.88 | 4.86 | 0.78 | 4.54 | 0.68 | 3.89 | 0.26 | 2.33 | 0.50 |
| MUSCLE | 0.36 | 0.05 | 0.29 | 0.04 | 0.22 | 0.05 | 0.18 | 0.05 | 0.13 | 0.04 |
| SKIN | 0.53 | 0.09 | 0.51 | 0.07 | 0.46 | 0.06 | 0.37 | 0.05 | 0.36 | 0.04 |
| BONE | 0.61 | 0.10 | 0.54 | 0.05 | 0.32 | 0.06 | 0.26 | 0.05 | 0.19 | 0.04 |
| LUNGS | 2.37 | 0.46 | 1.67 | 0.13 | 1.00 | 0.21 | 0.66 | 0.13 | 0.53 | 0.09 |
| HEART | 1.78 | 0.32 | 1.26 | 0.07 | 0.65 | 0.07 | 0.48 | 0.09 | 0.36 | 0.10 |
| BLOOD | 5.84 | 1.01 | 3.96 | 0.32 | 1.71 | 0.83 | 1.33 | 0.33 | 0.99 | 0.22 |
| URINE | — | — | — | — | — | — | — | — | 0.08 | 0.05 |
| STOMACH | 1.04 | 0.41 | 0.95 | 0.30 | 3.09 | 1.27 | 2.71 | 4.08 | 3.80 | 6.73 |
| TOT GIT | 0.61 | 0.08 | 0.74 | 0.26 | 1.59 | 0.63 | 2.62 | 0.70 | 5.16 | 1.86 |
| TAIL | 1.03 | 1.02 | 0.53 | 0.23 | 0.39 | 0.07 | 1.23 | 2.00 | 0.32 | 0.10 |

TABLE 4-continued

BIODISTRIBUTION OF $^{99m}$TC COMPLEX OF NO. 4[a]

| | MEAN 30 SEC | SD | MEAN 1 MIN | SD | MEAN 3 MIN | SD | MEAN 5 MIN | SD | MEAN 10 MIN | SD |
|---|---|---|---|---|---|---|---|---|---|---|
| BRAIN | 0.43 | 0.04 | 0.26 | 0.05 | 0.12 | 0.01 | 0.08 | 0.02 | 0.06 | 0.06 |
| THYROID | 3.49 | 0.83 | 2.28 | 0.25 | 1.11 | 0.63 | 0.89 | 0.24 | 0.79 | 0.18 |
| EYES | 0.22 | 0.03 | 0.19 | 0.05 | 0.15 | 0.04 | 0.13 | 0.08 | 0.16 | 0.04 |
| PANCREAS | 0.90 | 0.13 | 0.69 | 0.20 | 0.55 | 0.34 | 0.32 | 0.07 | 0.39 | 0.22 |
| THYMUS | 0.66 | 0.08 | 0.49 | 0.08 | 0.31 | 0.02 | 0.22 | 0.03 | 0.19 | 0.63 |

[a]Australian Albino Wistar Rats, % Injected dose per gram (X ± SD). Average of 5 animals per time point.

TABLE 5

BIODISTRIBUTION OF $^{99m}$TC COMPLEX OF NO. 5[a]

| | MEAN 30 SEC | SD | MEAN 1 MIN | SD | MEAN 3 MIN | SD | MEAN 5 MIN | SD | MEAN 10 MIN | SD |
|---|---|---|---|---|---|---|---|---|---|---|
| LIVER | 1.11 | 0.16 | 0.97 | 0.16 | 0.83 | 0.13 | 0.79 | 0.07 | 0.69 | 0.07 |
| SPLEEN | 0.83 | 0.12 | 0.98 | 0.10 | 0.83 | 0.08 | 0.83 | 0.05 | 0.72 | 0.03 |
| KIDNEYS | 4.35 | 0.55 | 5.70 | 0.45 | 4.70 | 0.10 | 6.04 | 1.92 | 3.61 | 0.36 |
| MUSCLE | 0.25 | 0.03 | 0.30 | 0.01 | 0.27 | 0.04 | 0.25 | 0.01 | 0.23 | 0.04 |
| SKIN | 0.31 | 0.03 | 0.38 | 0.06 | 0.43 | 0.04 | 0.41 | 0.09 | 0.46 | 0.04 |
| BONE | 0.37 | 0.02 | 0.45 | 0.02 | 0.42 | 0.03 | 0.37 | 0.08 | 0.36 | 0.03 |
| LUNGS | 1.66 | 0.19 | 1.69 | 0.20 | 1.31 | 0.09 | 1.25 | 0.15 | 1.17 | 0.10 |
| HEART | 1.81 | 0.22 | 1.62 | 0.18 | 1.24 | 0.09 | 1.15 | 0.11 | 1.06 | 0.17 |
| BLOOD | 4.92 | 0.67 | 4.22 | 0.34 | 3.26 | 0.29 | 3.13 | 0.17 | 2.59 | 0.19 |
| TAIL | 0.22 | 0.11 | 0.14 | 0.01 | 0.17 | 0.12 | 0.15 | 0.03 | 0.19 | 0.05 |
| BRAIN | 0.20 | 0.02 | 0.22 | 0.04 | 0.16 | 0.03 | 0.17 | 0.02 | 0.14 | 0.03 |
| THYROID | 1.85 | 0.31 | 2.43 | 0.67 | 1.59 | 0.46 | 1.73 | 0.45 | 1.71 | 0.29 |
| EYES | 0.17 | 0.01 | 0.23 | 0.03 | 0.19 | 0.03 | 0.18 | 0.02 | 0.18 | 0.02 |
| PANCREAS | 0.80 | 0.10 | 0.73 | 0.09 | 0.55 | 0.07 | 0.56 | 0.06 | 0.43 | 0.06 |
| THYMUS | 0.63 | 0.12 | 0.56 | 0.08 | 0.45 | 0.03 | 0.54 | 0.13 | 0.39 | 0.05 |
| STOMACH | 0.47 | 0.10 | 0.42 | 0.12 | 0.36 | 0.11 | 0.37 | 0.12 | 0.24 | 0.06 |
| TOT GIT | 0.35 | 0.04 | 0.34 | 0.04 | 0.31 | 0.04 | 0.29 | 0.06 | 0.27 | 0.02 |

[a]Australian Albino Wistar Rats, % Injected dose per gram (X ± SD). Average of 5 animals per time point.

| | COMPOUND NO. 6[a] | | | |
|---|---|---|---|---|
| | MEAN 3 MIN | SD | MEAN 5 MIN | SD |
| LIVER | 6.52 | 0.62 | 9.39 | 1.04 |
| SPLEEN | 2.24 | 0.42 | 1.78 | 0.15 |
| KIDNEYS | 24.05 | 3.93 | 18.35 | 0.89 |
| MUSCLE | 1.81 | 0.33 | 1.26 | 0.08 |
| SKIN | 3.96 | 0.41 | 3.47 | 0.39 |
| BONE | 1.91 | 0.02 | 1.39 | 0.11 |
| LUNGS | 6.38 | 1.04 | 4.66 | 0.39 |
| HEART | 3.84 | 0.62 | 2.80 | 0.38 |
| BLOOD | 10.65 | 0.87 | 7.83 | 0.54 |
| URINE | 1.30 | 0.88 | 0.95 | 0.43 |
| STOMACH | 1.78 | 0.38 | 6.85 | 6.36 |
| TOT GIT | 1.03 | 0.05 | 2.12 | 0.38 |
| TAIL | 8.94 | 3.42 | 6.18 | 2.50 |
| BRAIN | 0.74 | 0.21 | 0.35 | 0.11 |
| THYROID | 5.76 | 1.26 | 3.73 | 0.74 |
| PANCREAS | 1.86 | 0.18 | 1.41 | 0.22 |
| THYMUS | 3.67 | 1.03 | 2.50 | 0.41 |

[a]Balb/c mice, % Injected dose per gram (X ± SD). Average of 5 animals per time point.

TABLE 7

Biodistribution of Copper-67 complex of (5)

Biodistribution of: Ligand (5)-67Cu
Times: 1',3',5',10',30'.
Animals: 25 Balb/c mice.
Results: 4 Injected dose.

| % Inj Dose | 1 min | S.D. | 3 min | S.D. | 5 min | S.D. | 10 min | S.D. | 30 min | S.D. |
|---|---|---|---|---|---|---|---|---|---|---|
| Liver | 5.71 | 2.27 | 8.48 | 0.89 | 9.04 | 1.94 | 11.79 | 0.80 | 17.10 | 1.02 |
| Spleen | 0.18 | 0.11 | 0.19 | 0.03 | 0.16 | 0.04 | 0.16 | 0.02 | 0.19 | 0.03 |
| Kidney | 8.35 | 3.82 | 5.65 | 0.81 | 4.99 | 0.99 | 4.48 | 0.42 | 3.38 | 0.35 |

TABLE 7-continued

Biodistribution of Copper-67 complex of (5)

Biodistribution of: Ligand (5)-67Cu
Times: 1',3',5',10',30'.
Animals: 25 Balb/c mice.
Results: 4 Injected dose.

| % Inj Dose | 1 min | S.D. | 3 min | S.D | 5 min | S.D. | 10 min | S.D. | 30 min | S.D. |
|---|---|---|---|---|---|---|---|---|---|---|
| Muscle | 13.69 | 9.74 | 18.00 | 3.97 | 11.95 | 2.94 | 8.38 | 1.81 | 7.45 | 4.44 |
| Skin | 9.61 | 3.87 | 19.21 | 1.31 | 16.23 | 3.68 | 16.46 | 2.03 | 14.14 | 3.19 |
| Bone | 5.46 | 1.97 | 3.35 | 0.50 | 2.74 | 0.57 | 3.21 | 0.80 | 2.05 | 0.16 |
| Lung | 0.85 | 0.38 | 1.20 | 0.27 | 1.10 | 0.21 | 1.20 | 0.22 | 1.29 | 0.41 |
| Heart | 0.27 | 0.09 | 0.28 | 0.05 | 0.19 | 0.03 | 0.18 | 0.03 | 0.20 | 0.04 |
| Blood | 5.86 | 3.44 | 4.76 | 2.07 | 4.05 | 0.63 | 2.33 | 0.49 | 2.12 | 0.26 |
| Urine | 0.35 | 0.47 | 1.98 | 1.33 | 3.72 | 3.97 | 4.81 | 3.87 | 1.33 | 1.13 |
| Stomach | 0.52 | 0.22 | 0.93 | 0.15 | 0.87 | 0.26 | 0.80 | 0.41 | 1.22 | 0.26 |
| Tail | 8.27 | 9.95 | 5.19 | 4.72 | 5.36 | 2.39 | 3.45 | 2.23 | 1.51 | 0.47 |
| Pancreas | 0.20 | 0.13 | 0.11 | 0.03 | 0.12 | 0.04 | 0.34 | 0.22 | 0.34 | 0.05 |
| Brain | 0.23 | 0.12 | 0.22 | 0.02 | 0.23 | 0.09 | 0.19 | 0.15 | 0.54 | 0.88 |
| S. Int. | 0.50 | 0.23 | 1.10 | 0.23 | 1.08 | 0.24 | 0.90 | 0.48 | 0.71 | 0.32 |
| L. Int. | 0.35 | 0.14 | 0.75 | 0.26 | 0.54 | 0.15 | 0.79 | 0.25 | 0.31 | 0.15 |

We claim:

1. A compound consisting of a compound of the formula

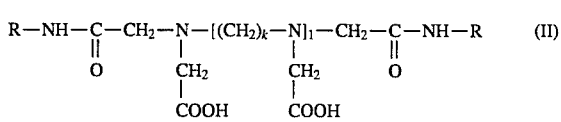

and the pharmaceutically acceptable salts thereof where k is an integer from 2 to 5 l is an integer from 1 to 5

R is independently selected from

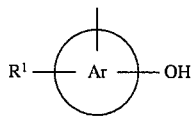

wherein Ar is an aryl or heteroaryl group;

$R^1$ is $-NR^2R^3$ where $R^2$ and $R^3$ are independently selected from hydrogen, $-(CH_2)_p-NH_2$; $-(CH_2)_p-Ar-(CH_2)_m-NH_2$; $-(CH_2)_p-CO_2H$; $-(CH_2)_p-Ar-CO_2H$; $-(CH_2CH_2O)_n-CH_2CH_2NH_2$; $-(CH_2)_p-NCS$, $-(CH_2)_p-Ar-NCS$; or $-(CH_2)_p NHCOR"$, $-COR"$; or $R^2$ and $R^3$ together with the nitrogen atom to which they are attached form an optionally substituted saturated or partially unsaturated ring optionally containing one or more heteroatoms O, S or N; or $R^1$ is $-NCS$, $-N=N$ or $-C(=NH)-OCH_3$;

n and m are independently an integer from 0 to 4 p is an integer from 1 to 4;

R" is alkyl-L where L is halogen; 2,5-diketo-pyrrolinyl, $-Het-CH=CH_2$ wherein Het is an optionally substituted 5 or 6 membered heterocyclic ring containing one or more heteroatoms O, N or S.

2. A pharmaceutical formulation comprising a compound of formula (II) as defined in claim 1 in a pharmaceutically acceptable carrier.

3. A compound of the formula:

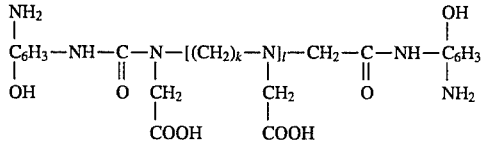

or the pharmaceutically acceptable salts thereof, wherein k is an integer from 2 to 5 and l is an integer from 1 to 5.

4. The compound of claim 3 wherein K is 2 and l is 1.

5. A pharmaceutical formulation comprising a compound of the formula

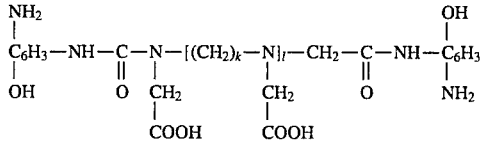

or a pharmaceutically acceptable salt thereof and a pharmaceutically acceptable carrier wherein k is an integer from 2 to 5 and l is an integer from 1 to 5.

6. The pharmaceutical formulation of claim 5 wherein in the compound k is 2 and l is 1.

* * * * *

UNITED STATES PATENT AND TRADEMARK OFFICE
CERTIFICATE OF CORRECTION

PATENT NO. : 5,550,160
DATED : Aug. 27, 1996
INVENTOR(S) : Smith, et al

It is certified that error appears in the above-indentified patent and that said Letters Patent is hereby corrected as shown below:

Cover page - Left hand column, Heading "OTHER PUBLICATIONS", - line 9, change "-N,n'-diacetic" to "-N,N'-diacetic"

Column 2, line 19 after "molybdenum-99" insert a space and —/—.

Column 3, line 23 after "$NH_2$;" insert "-$(CH_2)p$-$CO_2H$;"

Column 4, line 27 change "IN(III" to "In (III),"

- line 28, change "$TcO_4^{3-}$" to "$TcO_4^-$"

Column 7, TABLE A - heading change "$Ms^a$" to "$MS^a$"

sub column under heading "$NMR^d$ (ppm)" should read -
8.02, s,2H,OH; 6.91-6.72,m,6H; Ar; 3.46,
3.38, s, 4H, 4H, C$\underline{H}_2$CONH,C$\underline{H}_2$COOH
2.86, s,4H, NC$\underline{H}_2$C$\underline{H}_2$
9.63, s,2H,OH; 8.17, 8.01, 6.81, d, 6H, Ar;
3.45, 3.39,s, 4H, 4H, C$\underline{H}_2$CONH,C$\underline{H}_2$COOH
2.83, s,4H, NC$\underline{H}_2$C$\underline{H}_2$
9.88, s,2H,OH; 9.06, 7.89, 6.94, d, 6H, Ar;
3.56, 3.52, s, 4H, 4H, C$\underline{H}_2$CONH,C$\underline{H}_2$COOH
2.83, s,4H, NC$\underline{H}_2$C$\underline{H}_2$

UNITED STATES PATENT AND TRADEMARK OFFICE
CERTIFICATE OF CORRECTION

PATENT NO. : 5,550,160
DATED : Aug. 27, 1996
INVENTOR(S) : Smith, et al

It is certified that error appears in the above-indentified patent and that said Letters Patent is hereby corrected as shown below:

9.59, s,2H,OH; 8.11, 6.90, 6.75, d, 6H, Ar;
3.42, 3.38, s, 4H, 4H, C$\underline{H}_2$CONH,C$\underline{H}_2$COOH
2.86, s, 4H, NC$\underline{H}_2$C$\underline{H}_2$, 1.21, s, 18H, tBu;
9.33, s, 2H, OH; 8.41- 8.28, m, 6H, Ar;
5.42, 5.35, s, 4H, 4H, C$\underline{H}_2$CONH,C$\underline{H}_2$COOH
2.80, s, 4H, NC$\underline{H}_2$C$\underline{H}_2$

- line 55, change "bobohydride" to "borohydride".

- line 57, change "(10 ml/l ml)," to "(10 ml/l ml,"

Column 8, line 11 change "ITLC-9G" to "ITLC-SG".

Column 9, line 7 change "ITLC" to "ITLC-SG"

line 14 change "ITLC" to "ITLC-SG"

Column 10, line 2 change "11 hour" to "1 hour"

TABLE 1 - in heading change "TC" to "Tc"

Column 11, 12, 13 and 14

TABLE 2 - in heading change "TC" to "Tc"

UNITED STATES PATENT AND TRADEMARK OFFICE
CERTIFICATE OF CORRECTION

PATENT NO.  : 5,550,160
DATED       : Aug. 27, 1996
INVENTOR(S) : Smith, et al

It is certified that error appears in the above-indentified patent and that said Letters Patent is hereby corrected as shown below:

TABLE 3 - in heading    change "TC" to "Tc"

TABLE 4 - in heading    change "TC" to "Tc"

TABLE 4 continued - in heading    change "TC" to "Tc"

TABLE 5 - in heading    change "TC" to "Tc"

Column 13, at the end of table 5, insert heading -- TABLE 6 --

TABLE 6 - heading, change "COMPOUND NO. 6[a]" to "BIODISTRIBUTION OF $^{99m}$Tc COMPLEX OF NO. 6[a]"

Column 14, at the end of TABLE 5, change "-continued" to -- TABLE 6 continued --

TABLE 6 continued - heading, change "COMPOUND NO. 6[a]" , to "BIODISTRIBUTION OF $^{99m}$Tc COMPLEX OF NO. 6[a]"

TABLE 7 - line 5 (first column), change "Results: 4 Injected dose", to "Results: % Injected dose"

UNITED STATES PATENT AND TRADEMARK OFFICE
CERTIFICATE OF CORRECTION

PATENT NO. : 5,550,160
DATED : Aug. 27, 1996
INVENTOR(S) : Smith, et al

It is certified that error appears in the above-indentified patent and that said Letters Patent is hereby corrected as shown below:

(COMPARE THE FOLLOWING CHANGES TO TABLE 7 WITH LAYOUT FOR TABLES 4 AND 5)

- line 6 , column 8, delete "10"

- line 6 , column 10, delete "30"

- line 6, for columns, 3, 5, 7, 9 and 11 insert "S.D."

- line 6, for column 2, 4, 6, 8 and 10 insert "Mean"

- line 7, delete every occurrence of "S.D."

- line 7, centre "1 min" between columns 2 and 3
    centre "3 min" between columns 4 and 5
    centre "5 min" between columns 6 and 7

- line 7 column 8, replace "min" with -- 10 min -- centred between columns 8 and 9

- line 7 column 10, replace "min" with -- 30 min -- centred between columns 10 and 11

Column 15, TABLE 7 continued, line 5 (first column) change "Results: 4 Injected dose" to "Results: % Injected dose."

UNITED STATES PATENT AND TRADEMARK OFFICE
CERTIFICATE OF CORRECTION

PATENT NO. : 5,550,160
DATED : Aug. 27, 1996
INVENTOR(S) : Smith, et al

It is certified that error appears in the above-indentified patent and that said Letters Patent is hereby corrected as shown below:

- line 6 , column 8, delete "10"

- line 6 , column 10, delete "30"

- line 6, for columns, 3, 5, 7, 9 and 11 insert "S.D."

- line 6, for column 2, 4, 6, 8 and 10 insert "Mean"

- line 7, delete every occurrence of "S.D."

- line 7, centre "1 min" between columns 2 and 3
centre "3 min" between columns 4 and 5
centre "5 min" between columns 6 and 7

- line 7 column 8, replace "min" with -- 10 min -- centred between columns 8 and 9

- line 7 column 10, replace "min" with -- 30 min -- centred between columns 10 and 11

UNITED STATES PATENT AND TRADEMARK OFFICE
CERTIFICATE OF CORRECTION

PATENT NO. : 5,550,160
DATED : Aug. 27, 1996
INVENTOR(S) : Smith, et al

It is certified that error appears in the above-identified patent and that said Letters Patent is hereby corrected as shown below:

Column 16, line 41, change "K" to "k"

Signed and Sealed this

Fifth Day of May, 1998

Attest:

Attesting Officer

BRUCE LEHMAN

Commissioner of Patents and Trademarks